United States Patent
Jensen et al.

(10) Patent No.: US 7,235,079 B2
(45) Date of Patent: Jun. 26, 2007

(54) COMPOSITE BONE FASTENERS

(75) Inventors: David G. Jensen, Troutdale, OR (US); Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 246 days.

(21) Appl. No.: 10/993,205

(22) Filed: Nov. 18, 2004

(65) Prior Publication Data

US 2006/0106390 A1    May 18, 2006

(51) Int. Cl.
*A61B 17/56*    (2006.01)
(52) U.S. Cl. .................................................. 606/73
(58) Field of Classification Search ............ 606/72–73, 606/61, 69–71; 623/17.11, 17.16–17
See application file for complete search history.

(56) References Cited

U.S. PATENT DOCUMENTS

| | | | |
|---|---|---|---|
| 65,651 A | 6/1867 | Davies |
| 146,023 A | 12/1873 | Russell |
| 197,467 A | 11/1877 | Harvey |
| 197,933 A | 12/1877 | Harvey |
| 1,980,093 A | 11/1934 | Rosenberg |
| 2,146,023 A | 2/1939 | Lounsbury |
| 2,165,149 A | 7/1939 | Olson |
| 2,270,188 A | 1/1942 | Longfellow |
| 2,356,098 A | 8/1944 | Steinle et al. |
| 2,377,405 A | 6/1945 | Davies |
| 2,382,019 A | 8/1945 | Miller |
| 2,383,231 A | 8/1945 | Anderton |
| 2,419,555 A | 4/1947 | Fator |
| 2,621,145 A | 12/1952 | Sano |
| 2,633,091 A | 3/1953 | Wenger et al. |
| 2,801,631 A | 8/1957 | Charnley |
| 2,842,180 A | 7/1958 | Brown et al. |
| 3,051,169 A | 8/1962 | Grath |
| 3,079,181 A | 2/1963 | van der Wissel |
| 3,103,926 A | 9/1963 | Cochran et al. |
| 3,124,408 A | 3/1964 | Oestereicher |
| 3,233,500 A | 2/1966 | de Vellier |
| 3,454,070 A | 7/1969 | Phipard, Jr. |
| 3,664,540 A | 5/1972 | Witkin |
| 3,799,229 A | 3/1974 | Johnson |
| 3,915,162 A | 10/1975 | Miller |
| 4,058,856 A | 11/1977 | Doerre et al. |

(Continued)

FOREIGN PATENT DOCUMENTS

CA    731381    4/1966

(Continued)

OTHER PUBLICATIONS

*ReFractures After Forearm Plate Removal*, Rumball et al., *J. of Orthopaedic Trauma*, vol. 4, No. 2, pp. 124-129, 1990.

(Continued)

*Primary Examiner*—Eduardo C. Robert
*Assistant Examiner*—Anitza San Miguel
(74) *Attorney, Agent, or Firm*—Kolisch Hartwell, P.C.

(57) ABSTRACT

Systems, including apparatus, methods, and kits, with composite bone fasteners for fixing bones. The composite bone fasteners include an inner member or core for engagement with a driver and a bioresorbable outer member or sheath for threaded engagement with bone.

21 Claims, 3 Drawing Sheets

U.S. PATENT DOCUMENTS

| | | |
|---|---|---|
| 4,059,102 A | 11/1977 | Devas |
| 4,069,980 A | 1/1978 | Yarem et al. |
| 4,175,555 A | 11/1979 | Herbert |
| 4,259,072 A | 3/1981 | Hirabayashi et al. |
| 4,340,184 A | 7/1982 | Poss |
| 4,356,572 A | 11/1982 | Guillemin et al. |
| 4,394,370 A | 7/1983 | Jefferies |
| 4,440,750 A | 4/1984 | Glowacki et al. |
| 4,456,005 A | 6/1984 | Lichty |
| 4,463,753 A | 8/1984 | Gustilo |
| 4,468,200 A | 8/1984 | Munch |
| 4,537,185 A | 8/1985 | Stednitz |
| 4,550,449 A | 11/1985 | Tunc |
| 4,637,931 A | 1/1987 | Schmitz |
| 4,640,271 A | 2/1987 | Lower |
| 4,723,541 A | 2/1988 | Reese |
| 4,781,813 A | 11/1988 | Archer et al. |
| 4,842,464 A | 6/1989 | Green |
| 4,846,838 A | 7/1989 | Takai et al. |
| 4,854,311 A | 8/1989 | Steffee |
| 4,858,601 A | 8/1989 | Glisson |
| 4,863,383 A | 9/1989 | Grafelmann |
| 4,880,610 A | 11/1989 | Constantz |
| 4,882,149 A | 11/1989 | Spector |
| 4,892,429 A | 1/1990 | Giannuzzi |
| 4,898,186 A | 2/1990 | Ikada et al. |
| 4,917,554 A | 4/1990 | Bronn |
| 4,940,467 A | 7/1990 | Tronzo |
| 4,950,270 A | 8/1990 | Bowman et al. |
| RE33,348 E | 9/1990 | Lower |
| 4,959,064 A | 9/1990 | Engelhardt |
| 4,978,350 A | 12/1990 | Wagenknecht |
| 5,019,078 A | 5/1991 | Perren et al. |
| 5,019,079 A | 5/1991 | Ross |
| 5,042,982 A | 8/1991 | Harms et al. |
| 5,061,286 A | 10/1991 | Lyle |
| 5,067,963 A | 11/1991 | Khouri et al. |
| 5,073,373 A | 12/1991 | O'Leary et al. |
| 5,098,435 A | 3/1992 | Stednitz et al. |
| 5,108,399 A | 4/1992 | Eitenmuller et al. |
| 5,120,171 A | 6/1992 | Lasner |
| 5,122,133 A | 6/1992 | Evans |
| 5,139,499 A | 8/1992 | Small et al. |
| 5,147,363 A | 9/1992 | Harle |
| 5,169,400 A | 12/1992 | Mühling et al. |
| 5,180,382 A | 1/1993 | Frigg et al. |
| 5,234,430 A | 8/1993 | Huebner |
| 5,236,457 A | 8/1993 | Devanathan |
| 5,242,447 A | 9/1993 | Borzone |
| 5,252,016 A | 10/1993 | Schmid et al. |
| 5,259,398 A | 11/1993 | Vrespa |
| 5,284,655 A | 2/1994 | Bogdansky et al. |
| 5,290,558 A | 3/1994 | O'Leary et al. |
| 5,300,076 A | 4/1994 | Leriche |
| 5,306,275 A | 4/1994 | Bryan |
| 5,334,204 A | 8/1994 | Clewitt et al. |
| 5,356,629 A | 10/1994 | Sander et al. |
| 5,360,450 A | 11/1994 | Giannini |
| 5,364,400 A * | 11/1994 | Rego et al. ............ 606/72 |
| D356,868 S | 3/1995 | Broberg et al. |
| 5,397,572 A | 3/1995 | Coombes et al. |
| 5,403,136 A | 4/1995 | Mathys |
| 5,433,719 A | 7/1995 | Pennig |
| 5,454,811 A | 10/1995 | Huebner |
| 5,456,685 A | 10/1995 | Huebner |
| 5,470,334 A | 11/1995 | Ross et al. |
| 5,484,440 A | 1/1996 | Allard |
| 5,536,127 A | 7/1996 | Pennig |
| 5,562,672 A | 10/1996 | Huebner et al. |
| 5,569,252 A | 10/1996 | Justin et al. |
| 5,571,139 A | 11/1996 | Jenkins, Jr. |
| 5,584,836 A | 12/1996 | Ballintyn et al. |
| 5,593,410 A | 1/1997 | Vrespa |
| 5,645,547 A | 7/1997 | Coleman |
| 5,653,710 A * | 8/1997 | Harle ............ 606/73 |
| 5,676,667 A | 10/1997 | Hausman |
| 5,709,682 A | 1/1998 | Medoff |
| 5,709,686 A | 1/1998 | Talos et al. |
| 5,718,704 A | 2/1998 | Medoff |
| 5,725,529 A | 3/1998 | Nicholson et al. |
| 5,730,744 A | 3/1998 | Justin et al. |
| 5,733,307 A | 3/1998 | Dinsdale |
| 5,735,653 A | 4/1998 | Schiefer et al. |
| 5,743,912 A | 4/1998 | Lahille et al. |
| 5,743,914 A | 4/1998 | Skiba |
| 5,779,704 A | 7/1998 | Kim |
| 5,810,821 A | 9/1998 | Vandewalle |
| 5,827,285 A | 10/1998 | Bramlet |
| 5,827,287 A | 10/1998 | Tunc |
| 5,868,749 A | 2/1999 | Reed |
| 5,871,486 A | 2/1999 | Huebner et al. |
| 5,893,850 A * | 4/1999 | Cachia ............ 606/72 |
| 5,931,839 A | 8/1999 | Medoff |
| 5,941,878 A | 8/1999 | Medoff |
| 5,957,953 A | 9/1999 | DiPoto et al. |
| 5,964,767 A * | 10/1999 | Tapia et al. ............ 606/73 |
| 5,964,768 A | 10/1999 | Huebner |
| 5,968,046 A | 10/1999 | Castleman |
| 5,984,924 A | 11/1999 | Asher et al. |
| 6,001,101 A | 12/1999 | Augagneur et al. |
| 6,019,762 A | 2/2000 | Cole |
| 6,022,352 A | 2/2000 | Vandewalle |
| 6,030,162 A | 2/2000 | Huebner |
| 6,048,344 A | 4/2000 | Schenk |
| 6,077,266 A | 6/2000 | Medoff |
| 6,096,060 A | 8/2000 | Fitts et al. |
| 6,123,710 A | 9/2000 | Pinczewski et al. |
| 6,187,008 B1 | 2/2001 | Hamman |
| 6,231,606 B1 | 5/2001 | Graf et al. |
| 6,261,292 B1 | 7/2001 | Diebold et al. |
| 6,267,765 B1 | 7/2001 | Taylor et al. |
| 6,283,973 B1 | 9/2001 | Hubbard et al. |
| 6,299,615 B1 | 10/2001 | Huebner |
| 6,306,140 B1 | 10/2001 | Siddiqui |
| 6,319,254 B1 | 11/2001 | Giet et al. |
| 6,319,270 B1 | 11/2001 | Grafton et al. |
| 6,368,322 B1 | 4/2002 | Luks et al. |
| 6,368,326 B1 | 4/2002 | Dakin et al. |
| 6,393,950 B1 | 5/2002 | Crosser |
| 6,413,260 B1 | 7/2002 | Berrevoets et al. |
| 6,423,067 B1 | 7/2002 | Eisermann |
| 6,458,134 B1 | 10/2002 | Songer et al. |
| 6,461,373 B2 | 10/2002 | Wyman et al. |
| 6,468,278 B1 | 10/2002 | Muckter |
| 6,471,707 B1 | 10/2002 | Miller et al. |
| 6,517,542 B1 | 2/2003 | Papay et al. |
| 6,524,314 B1 | 2/2003 | Dean et al. |
| 6,537,274 B1 | 3/2003 | Katz |
| 6,569,186 B1 | 5/2003 | Winters et al. |
| 6,589,245 B1 | 7/2003 | Weiler et al. |
| 6,620,195 B2 | 9/2003 | Goble et al. |
| 6,629,977 B1 | 10/2003 | Wolf |
| 6,666,868 B2 | 12/2003 | Fallin |
| 6,685,728 B2 | 2/2004 | Sinnott et al. |
| 6,699,251 B1 | 3/2004 | Venturini |
| 6,811,552 B2 | 11/2004 | Weil, Sr. et al. |
| 6,875,216 B2 | 4/2005 | Wolf |
| 2001/0001119 A1 | 5/2001 | Lombardo |
| 2001/0053913 A1 | 12/2001 | Freedland |
| 2002/0013608 A1 | 1/2002 | ElAttrache et al. |
| 2002/0045900 A1 | 4/2002 | Harder et al. |
| 2002/0198527 A1 | 12/2002 | Muckter |
| 2003/0065332 A1 | 4/2003 | TenHuisen et al. |
| 2003/0074002 A1 | 4/2003 | West, Jr. |

| | | | |
|---|---|---|---|
| 2003/0088272 A1 | 5/2003 | Smith | |
| 2003/0105461 A1 | 6/2003 | Putnam | |
| 2003/0120280 A1* | 6/2003 | Roller et al. | 606/77 |
| 2003/0125744 A1 | 7/2003 | Contiliano et al. | |
| 2003/0130695 A1 | 7/2003 | McDevitt et al. | |
| 2003/0153918 A1 | 8/2003 | Putnam et al. | |
| 2003/0158555 A1 | 8/2003 | Sanders et al. | |
| 2004/0015172 A1 | 1/2004 | Biedermann et al. | |
| 2004/0172031 A1 | 9/2004 | Rubecamp et al. | |
| 2004/0210227 A1 | 10/2004 | Trail et al. | |
| 2004/0267361 A1* | 12/2004 | Donnelly et al. | 623/13.14 |
| 2005/0101961 A1 | 5/2005 | Huebner et al. | |
| 2005/0177165 A1 | 8/2005 | Zang et al. | |
| 2005/0187636 A1 | 8/2005 | Graham | |

FOREIGN PATENT DOCUMENTS

| | | |
|---|---|---|
| CA | 1007493 | 3/1977 |
| CH | 77837 | 6/1918 |
| CH | 643 131 A5 | 5/1984 |
| DE | 2618344 A1 | 11/1976 |
| DE | 3215228 A1 | 11/1983 |
| DE | 3630863 A1 | 3/1988 |
| DE | 4021550 A1 | 1/1991 |
| EP | 0 011 528 A1 | 5/1980 |
| EP | 0 172 130 B1 | 4/1989 |
| EP | 0 695 537 A1 | 2/1996 |
| EP | 0 471 334 B1 | 6/1997 |
| EP | 0 856 293 A1 | 8/1998 |
| FR | 2 588 332 A1 | 4/1987 |
| FR | 2 760 628 A1 | 3/1997 |
| GB | 598834 | 2/1948 |
| GB | 1389427 | 4/1975 |
| IT | 365613 | 12/1938 |
| IT | 598490 | 10/1959 |
| JP | 4-524729 | 8/1970 |
| JP | 6-233762 | 8/1994 |
| SU | 1034734 A | 8/1983 |
| SU | 1216466 A | 3/1986 |
| SU | 1718877 A1 | 3/1992 |
| WO | WO 89/09030 | 10/1989 |
| WO | WO 90/02526 | 3/1990 |
| WO | WO 91/09572 | 7/1991 |
| WO | WO 93/00518 | 1/1993 |
| WO | WO 98/40024 | 9/1998 |

OTHER PUBLICATIONS

The Herbert™ Bone Screws for Small Bone Fractures, Fracture Management, 97-1152-01 12.5MI printed in U.S.A. © 1992 Zimmer, Inc.
*A Comparison of Fixation Screws for the Scaphoid During Application of Cyclical Bending Loads*, Toby et al., *J. Bone and Joint Surg.*, vol. 79-A, No. 8, pp. 1190-1197, Aug. 1997.
*Acute Percutaneous Scaphoid Fixation*, Haddad et al., *J. Bone and Joint Surg.*, vol. 80-B, No. 1, pp. 95-99, Jan. 1998.
*Stabilization of Small Fragments and Intra-Articular Fractures, The Orthofix Fragment Fixation System*, The Orthofix, Inc., May 1998.
*Biomechanical Assessment of Compression Screws*, Wheeler et al., *Clinical Orthopaedics and Related Research*, No. 350, pp. 237-245, May 1998.
Clearfix Meniscal Screw instructional technique brochure, © 1998 Innovasive Devices, Inc.
*The Orthofix Fragment Fixation System Technical Monograph*, Orthofix, Mar. 1999.
*Conjure the Magic of Compression Pinning*, Orthofix, Oct. 1999.
*Conehead Wedging Screw for Distal Radius Fractures in Elderly Patients*, Shiota et al., *Clinical Orthopaedics and Related Research*, No. 407, pp. 203-210, 2003.
*Reduction and Association of the Scaphoid and Lunate for Scapholunate Ligament Injuries (RASL)*, Lipton et al., *Atlas Hand Clin*, vol. 8, pp. 249-260, 2003.
*Spin®—Snap—Off® Screw*, (Dec. 18, 2004), available at http://www.newdeal.info/ie5ps/produits/spin/spin.htm.
*T.A.C. 'pin®—Threaded Compression Pin*, (Dec. 18, 2004), available at http://www.newdeal.info/ie5ps/produits/tacpin/tacpin.htm.
*Fusion & Reconstructions System*, (Dec. 18, 2004), available at http://advancedwoundcare.com/images/FRS_System_ProdPic.jpg.

* cited by examiner

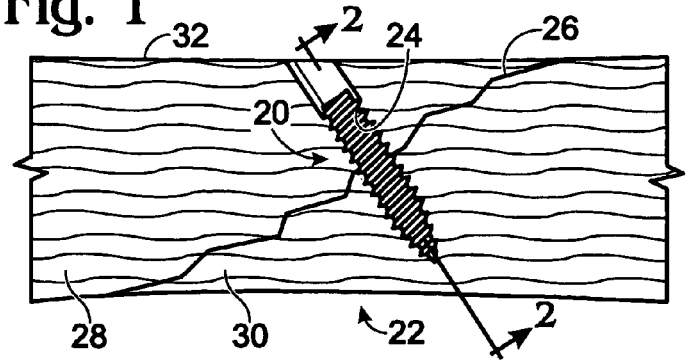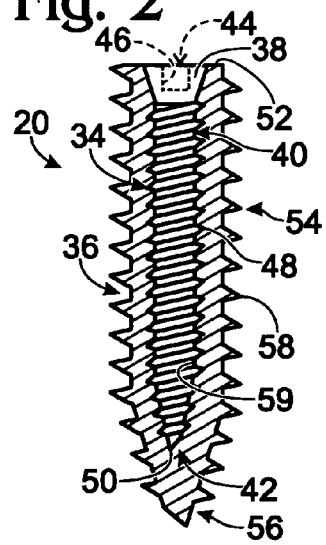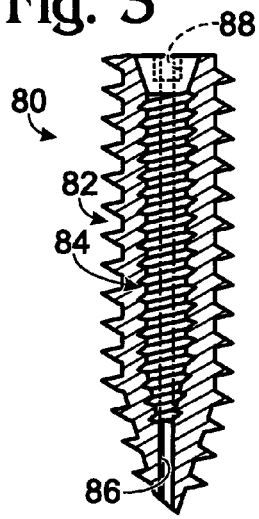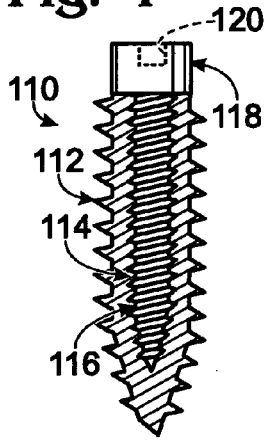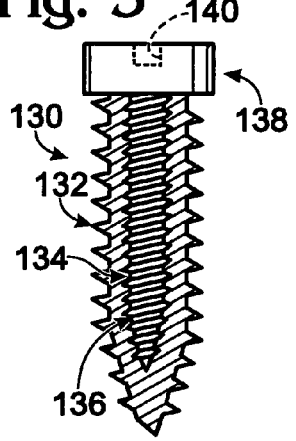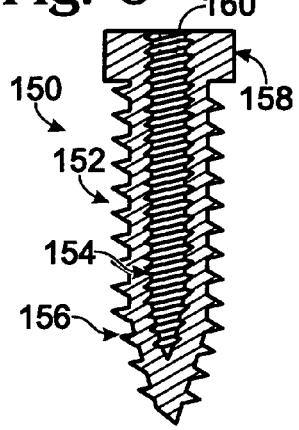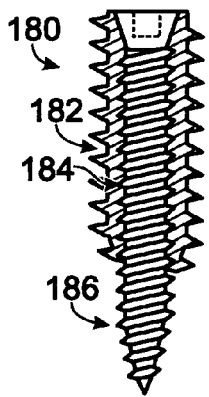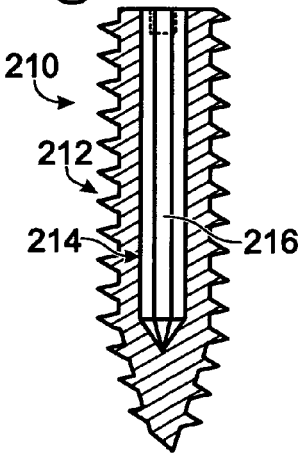

COMPOSITE BONE FASTENERS

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, fractured bones are treated using fixation devices, which reinforce the fractured bones and keep them aligned during healing. Fixation devices may take a variety of forms, including casts for external fixation, and bone plates and/or bone screws for internal fixation, among others.

Bone screws are threaded fasteners used to draw together and/or hold fragments of fractured bones. These screws may be used alone, for example, to span a fracture, and/or in combination with other fixation devices, for example, to secure a bone plate to a fractured bone on opposing sides of a fracture. To place a bone screw in bone, the bone screw is driven (e.g., turned) into a hole in bone, such that a thread of the bone screw engages the bone around the hole. The bone screw may be threaded along some or all of its length.

Some bone screws are made of bioresorbable materials that can be substantially broken down by the body. A bioresorbable bone screw allows the bone, with time, to grow inward into the hole occupied by the bone screw, to replace the bone that was removed when the hole was formed. Unfortunately, bioresorbable bone screws often are softer (weaker) than metal screws. Accordingly, bioresorbable bone screws may be more difficult to advance into bone without damaging the screws and/or may provide less strength to the bone during fixation. Moreover, because they are soft, these screws often are hollow along their length to provide additional surface area for engaging a driver, further reducing their strength.

SUMMARY

The present teachings provide systems, including apparatus, methods, and kits, for fixing bones with composite bone fasteners. The composite bone fasteners include an inner member or core for engagement with a driver and a bioresorbable outer member or sheath for threaded engagement with bone.

BRIEF DESCRIPTION OF THE DRAWINGS

FIG. 1 is a partially sectional view of an exemplary first composite bone fastener fixing a fractured bone, in accordance with aspects of the present teachings.

FIG. 2 is a partially sectional view of the composite bone fastener of FIG. 1, taken generally along line 2-2 in FIG. 1, with an outer member or sheath of the fastener represented in sectional view and an inner member or core of the fastener represented in nonsectional view, in accordance with aspects of the present teachings.

FIG. 3 is a partially sectional view of an exemplary second composite bone fastener for fixing a bone, in accordance with aspects of the present teachings.

FIG. 4 is a partially sectional view of an exemplary third composite bone fastener for fixing a bone, in accordance with aspects of the present teachings.

FIG. 5 is a partially sectional view of an exemplary fourth composite bone fastener for fixing a bone, in accordance with aspects of the present teachings.

FIG. 6 is a partially sectional view of an exemplary fifth composite bone fastener for fixing a bone, in accordance with aspects of the present teachings.

FIG. 7 is a partially sectional view of an exemplary sixth composite bone fastener for fixing a bone, in accordance with aspects of the present teachings.

FIG. 8 is a partially sectional view of an exemplary seventh composite bone fastener for fixing a bone, in accordance with aspects of the present teachings.

DETAILED DESCRIPTION

Figure 9:
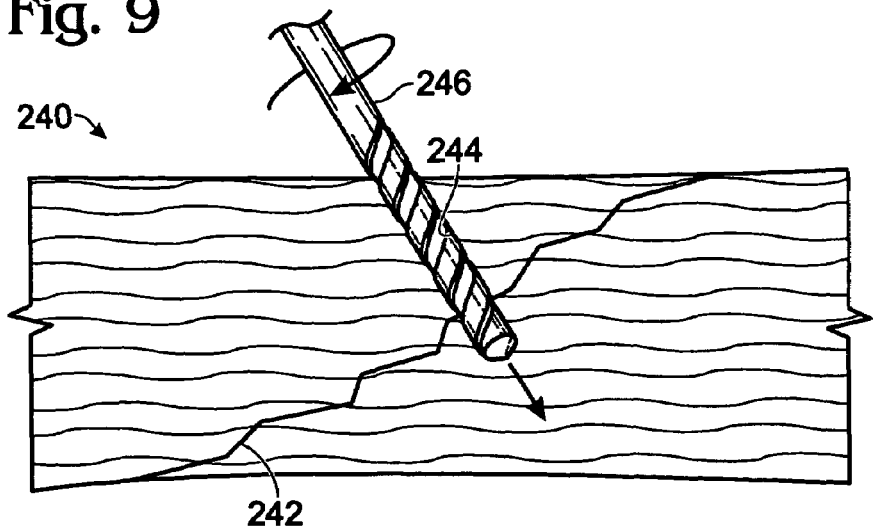
FIGS. 9-14 are partially sectional views of configurations of a bone, a composite fastener, and/or a drill produced before, during, and/or after performing steps of an exemplary method of fixing a bone, in accordance with aspects of the present teachings.

The present teachings provide systems, including apparatus, methods, and kits, for fixing bones with composite bone fasteners. The composite bone fasteners may include an inner member or core for engagement with a driver, and an outer member or sheath for threaded engagement with bone. The core may be formed of a material that is stronger (and/or less bioresorbable) than a material forming the sheath, so that the core can be turned effectively by the driver and/or persists longer in the body than the sheath. The sheath may be fixedly disposed around the core so that torque applied to the core is transmitted to the sheath. Accordingly, the composite fasteners of the present teachings may have sufficient strength to be driven into bone but may decrease in size over time by resorption to permit bone growth that reduces the amount of missing bone. In some examples, the core may include a threaded shank that facilitates optional removal of the core by rotation after selective resorption of the sheath. The composite bone fasteners of the present teachings thus may combine advantageous aspects of less resorbable and more resorbable bone fasteners.

Further aspects of the present teachings are included in the following sections, including, among others, (I) overview of composite bone fasteners; (II) methods of forming composite bone fasteners; (III) methods of using composite bone fasteners; (IV) kits with composite bone fasteners; and (V) examples.

I. Overview of Composite Bone Fasteners

FIG. 1 shows an exemplary composite bone fastener 20 fixing a fractured bone 22. Fastener 20 may be placed into (and/or concurrently form) a hole 24 in bone 22, so that the fastener spans at least one discontinuity in the bone, such as a fracture 26. Fastener 20 thus may be disposed in threaded engagement with proximal and/or distal bone pieces or fragments 28, 30 located on opposing sides of the fracture. The fastener may be placed at least substantially or completely inside bone 22, that is, inside a volume defined by the anatomical surface 32 of the bone. Alternatively, a portion of the fastener, such as a head, may be disposed at least partially or completely outside the bone.

FIG. 2 shows composite bone fastener 20 without the bone and in a partially sectional view. Fastener 20 may be configured generally as a bone screw having a core or inner member 34 and a sheath or outer member 36 disposed and/or around the core. In some examples, the sheath may be disposed fixedly on the core. The core and the sheath may be arranged concentrically. Further aspects of (A) cores and (B) sheaths are described below, with reference to FIG. 2 where appropriate or illustrative.

A. Cores

A core is any component of a fastener disposed partially or at least substantially inside a sheath or outer member of the fastener. The core may impart strength to the fastener, to permit a softer, weaker, and/or more bioresorbable sheath to be placed around a stronger, harder, and/or less bioresorbable core. (Generally, the strength of bioresorbable materials is related inversely to the rate at which they can be bioresorbed.) Strength, as used herein, is the maximum stress a material forming the core or sheath can withstand before fracture or breaking. The stress may be exerted to stretch the material (tensile stress), compress the material (compressive stress), shear or bend the material (shear stress), and/or twist the material (torsional stress). The core may be stronger than the sheath based on application of any one or more of these stresses, and particularly based on application of torsional stress. The core may have any suitable volume. In some examples, the volume of the core may be less than about two-thirds, or less than about one-half of the overall volume of the corresponding fastener. The core may include a proximal end region 38, an inner shank 40, and a distal tip region 42, among others.

The proximal end region of the core may have any suitable disposition and structure. For example, the proximal end region may define an external surface of the fastener or may be covered partially, substantially, or completely by the sheath. In some examples, the proximal end region may have a greater diameter than the inner shank of the core, thus forming a head of the core. Alternatively, the proximal end region may have about the same or a smaller diameter than the inner shank, so that the core is substantially headless. In addition, the proximal end region may define a driver engagement structure 44 configured to be engaged by a driver to advance the fastener into bone, such as by turning the fastener so that it threads into the bone. The driver engagement structure may be accessible from a proximal end of the fastener and/or may be configured to transmit torque from the driver to the fastener. Exemplary driver engagement structures may include a socket 46 (such as a polygonal (for example, hexagonal) socket), a protrusion, one or more holes, a transverse slot, a cruciform slot, and/or the like. Alternatively, or in addition, the sheath may define a driver engagement structure alone or in cooperation with the core.

The inner shank may have any suitable shape and disposition. The shape of the inner shank may be elongate, extending partially, substantially, or completely along the length of the sheath. The inner shank may be disposed at least partially or completely inside the sheath, generally with the sheath extending substantially or completely around the lateral surface of the inner shank. Accordingly, the inner shank may be shorter than, about the same length as, or longer than the sheath. In some examples, the inner shank and/or core is at least about one-half, or at least about five-eighths, or at least about three-fourths the length of the sheath, among others.

The inner shank may have any suitable diameter. Exemplary diameters may include about 0.5-5 mm, with particular examples of 1, 2, 3, and 4 mm. In some examples, the diameter of the inner shank may be less than about three-fourths, or less than about five-eighths, or less than about one-half the outer diameter of a corresponding overlying portion of the sheath. The inner shank may have a generally constant diameter and/or cross sectional geometry along a substantial portion of its length and/or may have a varying diameter and/or cross section, for example, tapering toward the distal end region (and/or the proximal end region) of the core. The inner shank may be generally cylindrical or noncylindrical. Exemplary noncylindrical inner shanks may have a transverse cross section that is polygonal (such as square, hexagonal, octagonal, etc.), elliptical, oval, rosette, etc. In some examples, noncylindrical inner shanks may have surface structure that facilitates holding the core in a fixed disposition within the sheath, such as knobs, dimples, grooves, and/or ridges, among others. The grooves and/or ridges may extend axially, circumferentially, obliquely, and/or the like. The inner shank may be substantially solid or may be partially or completely hollow. For example, the inner shank may have an axial bore extending along a substantial portion or all of its length, so that the inner shank (and the core) is cannulated.

The inner shank may include a thread, such as a male (exterior) thread 48, formed on the inner shank or may be nonthreaded externally. This thread may be complementary to a thread (e.g., a female (interior) thread) on an inner (receiving) surface of the sheath, such that the core may be unthreaded and removed from the sheath, before and/or after placement in the bone. Alternatively, the sheath may be disposed fixedly on the core, so that the core resists unthreading from the sheath until, for example, the sheath has been at least partially degraded/absorbed. The thread(s) on the inner shank may be a single thread or a plurality of axially offset, distinct threads disposed on interspersed, contiguous, and/or spaced regions of the inner shank. The thread may be left-handed or right-handed and may extend with the same handedness or opposite handedness to a thread formed on the sheath. The thread on the inner shank may extend along any suitable portion of the inner shank and/or core. In some examples, the thread may extend at least substantially from the proximal end region to the distal end region of the core, or may extend to a head of the core, if present. In some examples, the thread may be restricted to a proximal portion or a distal portion of the inner shank. The thread may have any suitable pitch, including a fixed or variable pitch. The pitch may correspond to a pitch of a thread on the sheath or may have a larger or smaller pitch. Exemplary thread pitches that may be suitable are described in the following patent application, which is incorporated herein by reference: U.S. Provisional Patent Application Ser. No. 60/548,685, filed Feb. 26, 2004. When nonthreaded (or threaded), the inner shank may include additional surface structure to restrict rotation relative to the sheath, as described above.

The distal tip region may have any suitable structure. For example, the distal tip region may be a blunt end created by a distal surface of a nontapered inner shank, or the distal tip region may taper relative to the inner shank, to create a sharp or rounded tip 50, among others. In some examples, the distal tip region may include a drilling structure (such as one or more axial teeth) and/or a tapping structure (such as axial flutes). The tapping structure may facilitate cutting a thread in the bone during placement of the fastener in bone and/or removal from the bone.

B. Sheaths

A sheath is any component of the fastener disposed on a core of the fastener. The sheath may extend at least substantially around the perimeter of the core and may at least substantially enclose the core. The sheath may be softer and/or weaker than the core and/or may be bioresorbable. The sheath may engage bone to hold the fastener in position when the fastener is first placed into bone. The sheath may have any suitable volume, such as at least about one-half the volume of the core or at least as great as the volume of the core. Accordingly, the sheath may have any suitable thickness on the core, but typically a thickness greater than about 0.1 mm or 0.2 mm, among others. The sheath may include a proximal end region 52, an outer shank 54, and a distal tip region 56, among others.

The proximal end region of the sheath may have any suitable size and shape. In some examples, this proximal end region may have a greater diameter than the outer shank, thus forming a head of the sheath and/or of the fastener. Alternatively, the proximal end region may have about the same or a smaller diameter than the outer shank, so that the sheath (and/or the fastener) is substantially headless or has a head formed by the core. The proximal end region may define a proximal surface disposed around the driver engagement structure of the fastener. Alternatively, or in addition, the proximal end region of the sheath may form at least a portion or all of the driver engagement structure.

The outer shank may have any suitable size and shape. Exemplary outer diameters for the outer shank may include about 0.5-10 mm, with particular examples of 1, 2, 3.5, 4.5, 5.5, and 6.5 mm. The outer shank may have a generally constant diameter along a substantial portion of its length and/or may have a varying diameter and/or cross section, for example, tapering toward the distal end region of the sheath. The outer shank may have an axial bore that extends completely or partially through the outer shank. The axial bore may be filled completely or incompletely (although generally substantially) with the core.

The outer shank may include a thread, such as a male thread 58, formed on the outer surface of the outer shank, or the outer shank may be nonthreaded externally. The outer shank also may include a thread, such as a female thread 59, on a inner (receiving) surface complementary to a thread, such as male thread 48, on the outer surface of the inner shank of the core. The inner surface of the outer shank may be formed during formation of the composite fastener, and may not exist prior to such formation. The thread(s) on the outer shank may be a single thread or a plurality of axially offset, distinct threads disposed on interspersed, contiguous and/or spaced regions of the outer shank. This thread may be left-handed or right-handed. This thread may extend along any suitable portion of the outer shank and/or sheath. In some examples, this thread may extend at least substantially along the entire length of the outer shank from the proximal end region to the distal end region of the sheath, or may extend to a head of the sheath, if present. In some examples, this thread may be restricted to a proximal portion or a distal portion of the outer shank. This thread may have any suitable pitch, including a fixed or variable pitch. Exemplary thread pitches that may be suitable are described in the following patent application, which is incorporated herein by reference: U.S. Provisional Patent Application Ser. No. 60/548,685, filed Feb. 26, 2004.

The distal tip region of the sheath may have any suitable structure. For example, the distal tip region may be a blunt end created by a distal surface of a nontapered outer shank, or the distal tip region may taper relative to the outer shank, to create a sharp or rounded tip, among others. In some examples, the distal tip region may include a drilling structure (such as one or more axial teeth) and/or a tapping structure (such as axial flutes).

C. Fastener Compositions

The core and the sheath may have any suitable composition. Each of the core and the sheath may be formed of the same, or more preferably, a different biocompatible material. Exemplary biocompatible materials that may be included in, and/or at least substantially may form, the core and/or sheath include (1) metals/metal alloys (for example, titanium or titanium alloys; alloys with cobalt, chromium, and/or molybdenum (such as cobalt-chrome); stainless steel; etc.); (2) plastics/polymers (such as ultra-high molecular weight polyethylene, polymethylmethacrylate (PMMA), polytetrafluoroethylene (PTFE), and/or PMMA/polyhydroxyethylmethacrylate (PHEMA)); (3) ceramics (for example, alumina, beryllia, and/or zirconia, among others); (4) bioresorbable polymers (such as polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, natural polymers (such as collagen or other polypeptides, polysaccharides (e.g., starch, cellulose, and/or chitosan), any copolymers thereof, etc.); and/or the like.

The core and/or sheath may be non-bioresorbable or may be formed at least substantially of a bioresorbable material, so that the core and/or sheath is at least substantially bioresorbable. A bioresorbable material, as used herein, is any material that is substantially broken down (degraded, dissolved, cleaved, and/or disintegrated, among others) over time in the body. Breakdown of the bioresorbable material may include and/or be followed by removal, restructuring, assimilation, and/or excretion, among others, of the broken-down material. In some examples, the bioresorbable material may be any material that is at least substantially replaced by bone during and/or after bioresorption. Replacement by bone may include macroscopically, microscopically, and/or atomically restructuring the bioresorbable material in situ and/or removing it. The bioresorbable material may be configured to be bioresorbed substantially over any suitable period of time, such as about one month, three months, six months, one year, two years, five years, or so on. In some examples, the sheath may be configured to be bioresorbed in a relatively shorter time, for example, less than about one year (such as less than about six months, among others), and the core may be configured to be bioresorbed in a relatively longer time, for example, greater than one year (such as about two years or five years or not at all, among others).

In some embodiments, the core and/or sheath may include or be formed at least substantially of a ceramic. The ceramic may be configured to be porous or nonporous. Exemplary ceramics include those listed above. In some embodiments, the ceramic may be osteoconductive, that is, able to serve as a scaffold on which bone cells may attach, migrate, and/or grow and divide. For example, the osteoconductive ceramic may include or be formed at least substantially of a glass (such as a bioglass formed of $SiO_2$, $Na_2O$, and/or $CaO$, among others). The glass may be configured so that bone attaches to the glass, such as by ingrowth into pores. In some examples, the osteoconductive ceramic may include and/or be formed substantially of calcium and/or phosphate. The calcium and phosphate may be in any suitable molecular form, such as amorphous calcium phosphate, monocalcium phosphate, dicalcium phosphate, tricalcium phosphate, octacalcium phosphate, hydroxyapatite, and/or composites thereof, among others. In exemplary embodiments, the ceramic includes or is formed at least substantially of tricalcium phosphate. The ceramic may be configured to be at least substantially bioresorbable. Generally, ceramics formed with calcium and phosphate are bioresorbable.

The core and/or sheath may include any suitable additives and/or fillers. In some examples, the core and/or sheath may include one or more osteoinductive substances. An osteoinductive substance, as used herein, is any substance that promotes stem cells, immature bone cells, and/or nonbone cell types to mature and/or differentiate into bone cells that facilitate laying down new bone. Exemplary osteoinductive substances that may be included in the core and/or sheath include bone morphogenetic proteins (such as BMP-1, BMP-2, BMP-3, etc.), Transforming Growth Factor-beta (TGF-β), Epidermal Growth Factor (EGF), Platelet Derived Growth Factor (PDGF), Fibroblast Growth Factors (FGFs), Parathyroid Hormone Related Peptide (PTHrp), Insulin-like Growth Factors (IGFs), and/or the like.

In some examples, the core may be formed of a material that makes the core stronger and/or intrinsically less bioresorbable than the sheath. The material of the core may be stronger because it is less malleable, less ductile, less plastic, more resistant to shear, and/or the like. In some examples, the core may be formed substantially of a bioresorbable ceramic or of a metal, and the sheath may include or be formed substantially of a bioresorbable polymer, a bioresorbable ceramic, and/or a blend thereof. In exemplary embodiments, the sheath may include or be formed substantially of a calcium/phosphate ceramic (such as tricalcium phosphate) as filler disposed in a bioresorbable polyester matrix (formed, for example, with poly-L-lactic acid).

II. Methods of Forming Composite Bone Fasteners

The composite bone fasteners of the present teachings may be formed by any suitable methods, generally according to the composition and structure of the fasteners. Exemplary methods of forming the core and the sheath are presented below.

The core may be formed of metal by standard methods of forming bone screws. For example, a metal core, with or without a thread or tool-engagement structure, may be formed by casting, machining a nonthreaded shaft, cold- and/or hot-forming, and/or the like.

The core may be formed of ceramic by any suitable methods. In exemplary embodiments, a calcium-phosphate material (such as hydroxyapatite and/or tricalcium phosphate, among others) may be obtained in a particulate configuration and/or a paste, shaped according to the desired form of the core (such as by placement into a mold), and then sintered by application of heat (such as by heating the shaped core to a temperature of at least about 1000° C. for at least about one hour). Alternatively, or in addition, the ceramic may be machined to finish the core, for example, to form a thread and/or a tool-engagement structure on the core.

A sheath including a bioresorbable matrix may be formed on a pre-formed core. In particular the sheath may be molded around the core (such as by injection molding) to produce a final form of the sheath, and/or machined after formation of a proto-sheath on the core. The bioresorbable matrix may be polymerized in situ around the core, such as by solid-state polymerization. Alternatively, or in addition, the polymer may be synthesized separately, melted by heating, molded around the core, and then cooled to a solidified state. In some examples, the sheath may be formed from a blend of a bioresorbable polymer (or polymer precursor) and a particulate ceramic as filler. Creation of the polymer matrix may thus trap the particulate ceramic in the sheath.

III. Methods of Using Composite Bone Fasteners

Composite bone fasteners may be used on any suitable bone(s), in any suitable species, including human, equine, canine, and/or feline species, among others. Exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, ribs, and/or clavicles, among others.

Composite bone fasteners may be used for any suitable purpose in and/or adjacent the bone(s). For example, the bone fasteners may be configured to span any suitable bone discontinuity (or discontinuities) so that the fasteners fix the relative positions of bone pieces/fragments (and/or bones) disposed on opposing sides of the bone discontinuity (or discontinuities). In some embodiments, the bone fasteners may reinforce a bone lacking a discontinuity. Alternatively, or in addition, the bone fasteners may be used in conjunction with a fixation device, such as a bone plate.

Suitable discontinuities may occur naturally and/or may result from injury, disease, and/or surgical intervention, among others. Accordingly, exemplary discontinuities for use with the composite bone fasteners described herein may include joints, fractures (breaks in bones), osteotomies (cuts in bones), and/or nonunions (for example, produced by injury, disease, or a birth defect), among others.

The methods of the present teachings may be used to fix bones. Exemplary methods may include any suitable combination of the steps described in the following paragraphs, performed in any suitable order, any suitable number of times.

A bone for fixation may be selected. Suitable bones and discontinuities are described above. In the case of a fractured bone, the fracture may be reduced before, during, and/or after placement of composite bone fasteners.

One or more composite bone fasteners, such as bone screws, may be selected for placement into the bone. Each composite bone fastener may have a stronger core and a softer, more bioresorbable sheath. The size and number of the bone fasteners may be selected, for example, based on the size (such as the diameter) of the bone to fixed and/or based on the size/severity/disposition of the fracture. One or more noncomposite bone fasteners also may be selected. In some examples, a bone fixation device, such as a bone plate, may be selected according to the bone to be fixed.

At least one hole may be formed in the bone. The number of holes formed may correspond to the number of composite bone fasteners selected. The hole(s) may extend across a fracture in the bone or may terminate at or before the fracture. The hole(s) may be formed using a hole-forming device, such as a drill. Alternatively, or in addition, the hole(s), or some of the holes among a plurality of holes, or portions of any given hole, may be formed by the bone fasteners themselves, particularly self-tapping bone fasteners, during their placement into the bone. The hole may be tapped (threaded) or may be nontapped (nonthreaded). The hole may have any suitable size. In some examples, the hole may have a diameter less than the diameter of the composite bone fasteners selected, or may have a diameter corresponding substantially to the diameter of the bone fasteners (such as when the hole is also tapped). Furthermore, the hole may have a depth that is less than, about the same as, or, greater than the length of a composite bone fastener.

Each composite bone fastener may be placed into a corresponding hole in the bone. A driver may engage the core of each fastener to rotate each fastener and thus advance the fastener into threaded engagement with the bone around the hole. The fastener may be buried in the bone, may be flush with the bone, or a proximal and/or distal end of the fastener may protrude above the bone surface.

Each composite bone fastener may be left in the bone for any suitable length of time. In some examples, one or more of the bone fasteners may be left in the bone until at least about one-third or one-half of the volume of the bone fastener has been selectively resorbed. In some examples, this resorption may be selective for the sheath. In some embodiments, such selective resorption may take at least about one month or longer. In some embodiments, a fracture of the bone may heal at least substantially before the selective resorption is complete. Selective resorption may replace the sheath with new bone. In some examples, the core of one or more of the composite bone fasteners may be removed from the bone selectively (generally without the sheath) during and/or after selective resorption of the sheath. Removal may be performed by unthreading the core from new bone formed around the core and/or from degrading/degraded sheath around the core. The core may be removed to reduce problems, such as irritation, caused by the core and/or to remove a nonresorbable core from the bone. Alternatively, or in addition, one or more of the cores may be left in the bone until they are at least substantially resorbed by the body.

Further aspects of methods of using composite bone fasteners to fix bones are included below in Example 2.

IV. Kits with Composite Bone Fasteners

The systems of the present teachings may provide kits for fixing bones. These kits may include (1) one or more composite bone screws, (2) one or more drivers for placing and/or removing the bone screws, (3) one or more drills and/or taps to form suitably structured holes for receiving the bone screws, (4) additional noncomposite bone screws, and/or (5) instructions for use of the kit components, among others.

The composite bone screws may have any suitable size, condition, and arrangement within a kit. The composite bone screws (or cores/sheaths thereof) may be of the same or different diameters, lengths, core-to-sheath volume ratios, etc. The composite bone screws may be packaged in a sterile condition, or they may be nonsterile when supplied. Nonsterile bone screws may be subjected to a sterilization step, for example, washing and/or autoclaving, prior to placement in bone. The bone screws may be arranged according to size, intended use, etc.

The kits also may include additional tools and/or consumable surgical supplies that may be required for carrying out connective tissue repair, such as clamps, sutures, staples, wires, and/or other surgical tools that may facilitate grasping and/or positioning the connective tissue that is being repaired.

The kits may be constructed or assembled for single and/or multiple use. For example, the kits, or components thereof, may be configured, in some embodiments, for a single use, such as fixing a single bone, during a single surgical procedure. These embodiments optionally may be prepackaged in a sterile wrapper. Thus, as needed, components of the kit could be removed from the sterile wrapper, used to form holes and drive bone screws, and then discarded. Alternatively, the kits, or components thereof, may be configured, in other embodiments, for effecting multiple repairs, during the same or different surgical procedures. In these cases, reusable components (particularly drivers and/or drills) may be configured to reduce contamination (e.g., via smooth surfaces) and/or to facilitate sterilization, such as by washing and autoclaving (e.g., through choice of material, such as metal).

V. EXAMPLES

The following examples describe selected aspects of the present teachings, including exemplary composite bone fasteners and exemplary methods of using composite bone fasteners. These examples are included for illustration and are not intended to limit or define the entire scope of the present teachings.

Example 1

Exemplary Composite Bone Screws

This example describes exemplary composite bone screws that may be constructed according to the present teachings; see FIGS. 3-8.

FIG. 3 shows an exemplary composite bone screw 80 that is cannulated. Bone screw 80 may include a threaded sheath 82 disposed around a threaded core 84. The bone screw may be cannulated, for example, having an axial bore 86 that extends through the core and the sheath, for example, coaxial with a socket 88 of the core for receiving a driver. The axial bore may receive a guide wire that directs the bone screw into bone.

FIG. 4 shows another exemplary composite bone screw 110. Bone screw 110 may include a threaded sheath 112 disposed around a threaded core 114, particularly an inner shank 116 thereof. The core also may include a head 118 disposed proximally to the inner shank. The head may include a socket 120 for receiving a driver. Furthermore, the head may have a diameter that is less than the maximum diameter of sheath 112, for example, a diameter that is about the same as the root-to-root diameter of the sheath. Accordingly, the screw may be threaded flush with and/or interior to a bone plate or bone, without the head catching on or otherwise being blocked by the bone plate or bone.

FIG. 5 shows yet another exemplary composite bone screw 130. Bone screw 130 may include a threaded sheath 132 disposed around a threaded core 134, particularly an inner shank 136 thereof. The core also may include a head 138 disposed proximally to the inner shank. The head may include a socket 140 for receiving a driver. Furthermore, the head may have a diameter that is greater than the maximum diameter of the sheath 132. Accordingly the head may be configured to engage an anatomical surface of bone, a counterbore formed in the bone, and/or a bone-repair device (or a counterbore formed therein) (such as a bone plate or prosthesis, among others).

FIG. 6 shows still another exemplary composite bone screw 150. Bone screw 150 may include a threaded sheath 152 disposed around a threaded core 154. The sheath may include an outer shank 156 disposed distally, and a head 158 disposed proximally. The head may have a greater diameter than the outer shank and may be threaded or nonthreaded. The head may extend to a position flush with the proximal end 160 of the core or may extend proximally thereof, so that the core is recessed proximally. The head may be configured to engage an anatomical surface of bone, a counterbore formed in the bone, and/or a bone-repair device (or a counterbore formed therein), among others.

FIG. 7 shows yet another exemplary composite bone screw 180. Bone screw 180 may include a threaded sheath 182 disposed around a threaded core 184. The sheath may be shorter than the core, so that a distal portion 186 of the core extends distally out of the sheath to an exposed position in the bone screw.

FIG. 8 shows still another exemplary composite bone screw 210. Bone screw 210 may include a threaded sheath 212 disposed around a nonthreaded core 214. Nonthreaded core may have a faceted lateral surface 216, flutes, rugosities, and/or other features configured to restrict rotation of the core relative to the sheath.

Example 2

Exemplary Methods of Fixing Bones with Composite Bone Screws

This example describes exemplary methods of fixing bones with composite bone screws; see FIGS. 9-14.

FIG. 9 shows a fractured bone 240 with a fracture 242 and a hole 244 being formed across the fracture. Hole 244 may be formed with a drill 246 and/or a tap device and may have a nonthreaded or threaded wall. In some examples, a self-drilling and/or self-tapping bone screw may be used to form its own hole, instead of, or in addition to, a drill and/or a tap device.

Figure 10:
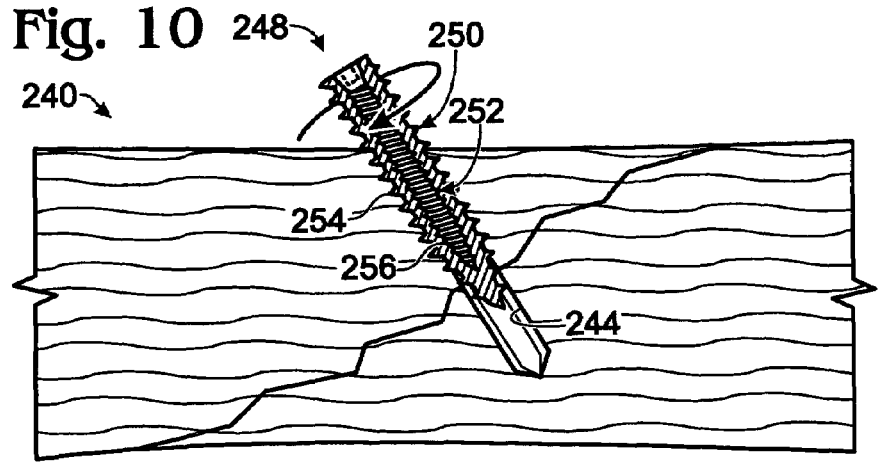

FIG. 10 shows a composite bone screw 248 being placed into bone 240, particularly hole 244, which may be formed before and/or during placement of the bone screw into the bone. Composite bone screw 248 may include a threaded sheath 250 substantially enclosing a threaded core 252. Sheath 250 may be formed of a more bioresorbable material 254 that is softer and/or weaker than a less bioresorbable material 256 forming the core. The bone screw may be engaged through core 252 and rotated into the bone, so that the threaded sheath engages the bone around hole 244.

Figure 11:
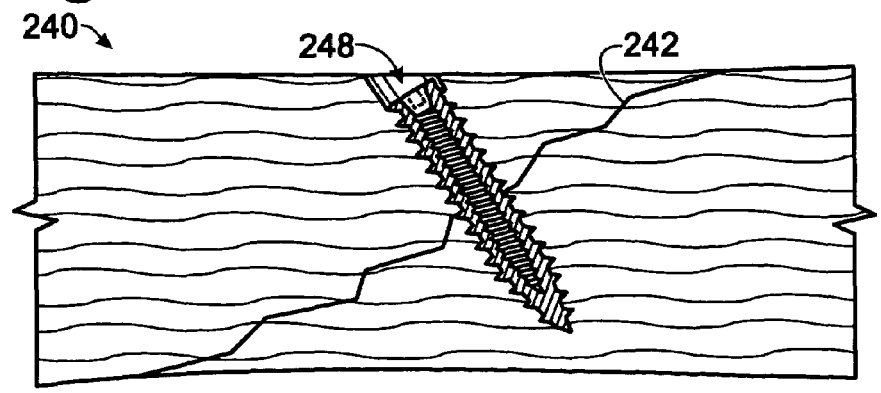

FIG. 11 shows composite bone screw 248 buried in bone 240 and spanning fracture 242 to fix the bone. This configuration may be obtained using any suitable procedure, for example, following the configurations shown in FIGS. 9 and 10, among others. In some embodiments, a plurality of composite bone screws may be placed into the bone to fix the bone, using the illustrated and/or different procedures.

Figure 12:
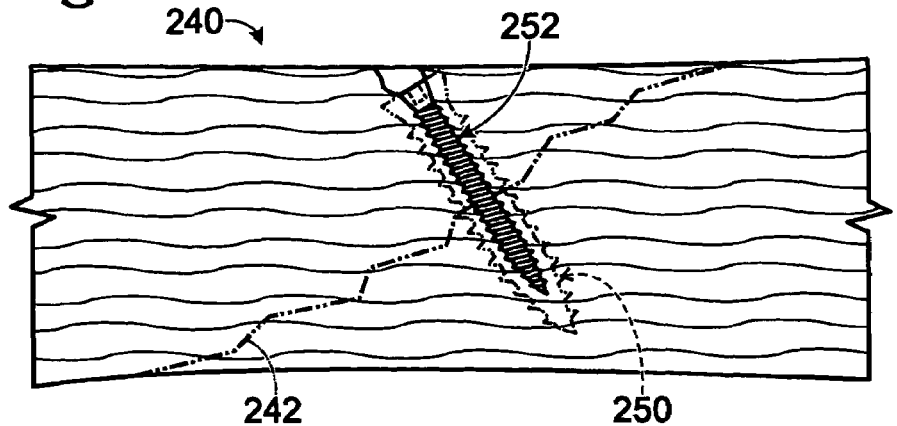

FIG. 12 shows bone 240 after fracture 242 (shown dashed) has healed substantially, and sheath 250 (shown in phantom outline) of the bone screw has been resorbed substantially and replaced by new bone. Core 252 may be substantially nonresorbed at this stage.

Figure 13:
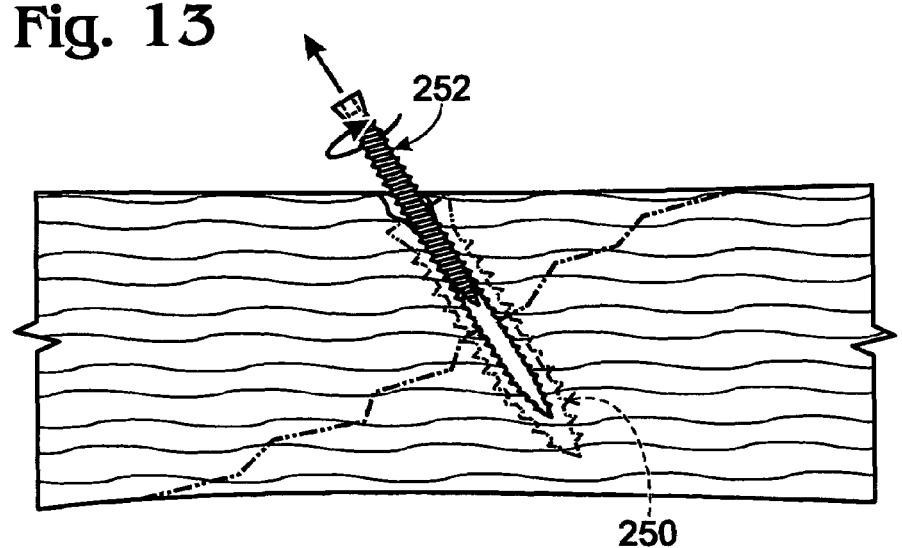

FIG. 13 shows optional removal of core 252 after sheath 250 has been at least partially selectively resorbed. The core may be engaged with a driver and unthreaded from the bone. Generally, this step may be performed at any suitable time, typically after at least partial resorption of sheath 250. Waiting until the sheath is at least partially resorbed may facilitate any strengthening function performed by the core and/or make it easier to unthread the core from the sheath and/or new bone.

Figure 14:
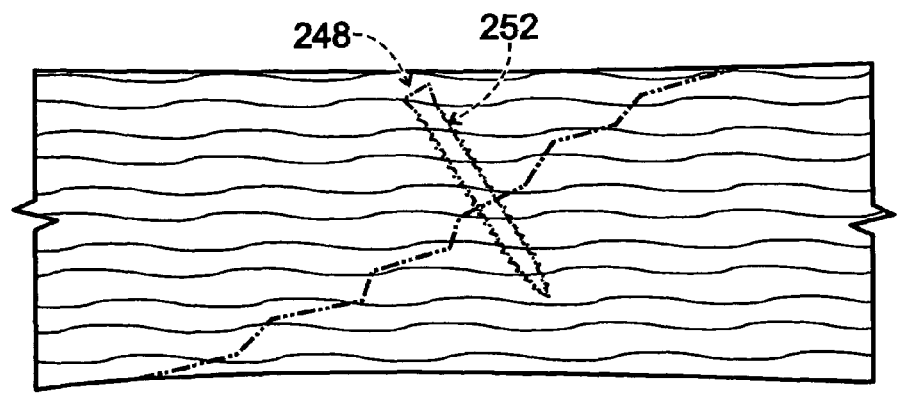

FIG. 14 shows resorption of core 252 (shown in phantom outline) and thus substantially complete resorption of bone screw 248. In this case, the core has not been removed (in contrast to FIG. 13), but has been left in the bone to be resorbed instead.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A fastener for placement into bone, comprising:
an inner member including a shank having an external thread, the inner member also including a driver engagement structure configured to transmit torque to the fastener from a driver, the inner member having a volume; and
an outer member including a shank having an external thread, the shank of the outer member being disposed around and contacting the shank of the inner member, the outer member being at least substantially bioresorbable and having a volume that is at least about one-half the volume of the inner member,
wherein the outer member is disposed fixedly on the inner member during fabrication of the fastener such that the outer member does not turn relative to the inner member.

2. The fastener of claim 1, wherein the volume of the outer member is greater than the volume of the inner member.

3. The fastener of claim 1, wherein the inner member is at least substantially bioresorbable.

4. The fastener of claim 1, wherein the inner member is formed of a first material and the outer member is formed of a second material, and wherein the first material is stronger than the second material.

5. The fastener of claim 4, wherein the second material is configured to be bioresorbed more rapidly than the first material.

6. The fastener of claim 1, wherein each of the inner and outer members includes a ceramic.

7. The fastener of claim 6, wherein the ceramic includes calcium and phosphate.

8. The fastener of claim 1, wherein the outer member includes a calcium-phosphate ceramic and a bioresorbable polymer.

9. The fastener of claim 1, wherein the inner member has a proximal end adjacent the driver engagement structure and a distal end opposing the proximal end, and wherein the outer member extends at least substantially from the proximal end to a position beyond the distal end of the inner member.

10. The fastener of claim 1, wherein each of the inner member and the outer member has a maximum diameter, and wherein the maximum diameter of the outer member is greater than the maximum diameter of the inner member.

11. The fastener of claim 1, each of the inner and outer members having a length, wherein the length of the inner member is greater than half the length of the outer member.

12. The fastener of claim 1, wherein the outer member includes a bioresorbable polymer.

13. The fastener of claim 12, wherein the bioresorbable polymer includes a polyester.

14. The fastener of claim 1,
wherein each of the inner member and the outer member has a maximum diameter, and wherein the maximum diameter of the outer member is greater than the maximum diameter of the inner member.

15. The fastener of claim 1, wherein the fastener further comprises a tip opposing the driver engagement structure, and wherein the outer member tapers toward the tip along at least a portion of the outer member.

16. A method of fixing a bone, comprising:
selecting a fastener having an inner member and an outer member disposed around and contacting the inner member
advancing the outer member into threaded engagement with the bone by rotation of the inner member using a driver engaged with the inner member;
leaving the fastener in the bone until the outer member is at least partially resorbed; and
unthreading the inner member selectively from the bone after the step of leaving so that the inner member is removed from the bone.

17. The method of claim 16, further comprising steps of drilling and tapping a hole in the bone before the step of advancing, wherein the step of advancing positions the fastener into the hole.

18. The method of claim 16, wherein the step of advancing disposes at least substantially all of the fastener inside the bone.

19. The method of claim 16, wherein the step of selecting a fastener includes a step of selecting a fastener having an outer member fixedly disposed on an inner member.

20. The method of claim 16, wherein the step of advancing includes a step of advancing the fastener into a fractured bone, and wherein the step of unthreading is performed after the fractured bone has healed at least substantially.

21. The method of claim 16, wherein the step of unthreading is performed after the outer member has been replaced substantially with new bone.

* * * * *